US 8,263,554 B2

(12) United States Patent
Tatarkiewicz et al.

(10) Patent No.: US 8,263,554 B2
(45) Date of Patent: Sep. 11, 2012

(54) METHODS OF USING GLP-1 RECEPTOR AGONISTS TO TREAT PANCREATITIS

(75) Inventors: Krystyna Tatarkiewicz, San Diego, CA (US); David G. Parkes, Del Mar, CA (US); Denis Roy, Vista, CA (US); Bronislava Gedulin, Del Mar, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/155,211

(22) Filed: Jun. 7, 2011

(65) Prior Publication Data

US 2011/0306549 A1    Dec. 15, 2011

Related U.S. Application Data

(60) Provisional application No. 61/352,906, filed on Jun. 9, 2010.

(51) Int. Cl.
*A61K 38/26* (2006.01)
*A61P 3/10* (2006.01)
*A61P 7/12* (2006.01)

(52) U.S. Cl. .................................... 514/11.7
(58) Field of Classification Search .................. None
See application file for complete search history.

(56) References Cited

U.S. PATENT DOCUMENTS

| 6,852,690 B1 | 2/2005 | Nauck et al. |
| 7,569,540 B2 | 8/2009 | Nauck et al. |
| 2009/0142338 A1 | 6/2009 | Levetan |
| 2010/0069309 A1* | 3/2010 | Gage .......................... 514/18 |
| 2011/0256130 A1* | 10/2011 | Schultz et al. ............. 424/133.1 |
| 2011/0268795 A1* | 11/2011 | Fayad ......................... 424/457 |

OTHER PUBLICATIONS

Amylin Pharmaceuticals, Inc., Byetta® Prescribing Information (May 2010).
Brubaker, *Endocrinology* 151(5):1984-1989 (May 2010): Minireview: Update on Incretin Biology: Focus on Glucagon-Like Peptide-1.
Nachnani et al., *Diabetologia* 53:153-159 (2010): Biochemical and histological effects of Exendin-4 (exenatide) on the rat pancreas.
Noel, R.A., et al., *Diabetes Care* 32(5):834-838 (May 2009): Increased risk of acute pancreatitis and biliary disease observed in patients with type 2 diabetes: a retrospective cohort study.
Tatarkiewicz et al., *Am. J. Physiol. Endocrinol. Metab.* 299:E1076-E1086 (2010): Exenatide does not evoke pancreatitis and attenuates chemically induced pancreatitis in normal and diabetic rodents.
Wang et al., *World J. Gastroenterol.* 15(12):1427-1430 (Mar. 2009): Acute pancreatitis: etiology and common pathogenesis.
Koehler et al. "Glucagon-like peptide-1 receptor activation modulates pancreatitis-associated gene expression but does nott modify the susceptibility to experimental pancreatitis in mice." *Diabetes*, Jun. 2009, vol. 58: p. 2148-2161.
Hansen et al. "Incretin mimetics: a novel therapeutic option for pationtts with type 2 diabetes-a review" Diabetes, Metabolic Syndrome and Obesity: Targets and Therapy; May 14, 2010; vol. 3; p. 155-163.
International Search Report and Written Opinion for PCT Application No. PCT/US11/39494 dated Feb. 9, 2012.

* cited by examiner

*Primary Examiner* — Robert Landsman
(74) *Attorney, Agent, or Firm* — Kilpatrick Stockton & Townsend LLP

(57) ABSTRACT

The disclosure provides the use of GLP-1 receptor agonist compounds to treat pancreatitis (e.g., acute, chronic, hemorrhagic, necrotizing) in patients. The disclosure also provides the use of GLP-1 receptor agonist compounds to reduce elevated plasma amylase and/or lipase concentrations in patients. An exemplary GLP-1 receptor agonist compound is exenatide.

18 Claims, 2 Drawing Sheets

METHODS OF USING GLP-1 RECEPTOR AGONISTS TO TREAT PANCREATITIS

RELATED APPLICATIONS

This application claims priority to U.S. Application No. 61/352,906 filed Jun. 9, 2010, the disclosure of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jun. 29, 2011, is named 249USUTL.txt and is 38,333 bytes in size.

FIELD

Provided herein are methods to treat pancreatitis using Glucagon-Like Peptide-1 (GLP-1) receptor agonist compounds.

BACKGROUND

When compared to the general population, patients with Type 2 diabetes are at increased risk of developing numerous other health problems, including heart disease, cancer, and pancreatitis.

Type 2 diabetics have a 2-fold to 4-fold greater risk of developing coronary heart disease than the general population. Haffner, *The Journal of Clinical Endocrinology & Metabolism,* 85(6):2108-2110 (2000). Type 2 diabetics are also at increased risk of developing twenty-four different types of cancer including cancers of the pancreas, liver, kidneys, thyroid, esophagus, small intestine, and nervous system. For example, Type 2 diabetics have a 6-fold greater risk and a 4.25-fold greater risk of developing pancreatic cancer and liver cancer, respectively, when compared to the general population. German Cancer Research Center Press Release dated May 20, 2010.

Type 2 diabetics have a 2.8-fold greater risk of developing pancreatitis when compared to the general population. Noel et al., "Increased Risk of Acute Pancreatitis and Biliary Disease Observed in Patients With Type 2 Diabetes," *Diabetes Care,* 32(5):834-838 (2009). Pinhas-Hamiel et al., "Acute necrotizing pancreatitis in an adolescent with type 2 diabetes," *Current Opinion in Pediatrics,* 18(2):206-208 (2006). The severity of pancreatitis can vary from a mild form to life threatening multiple-organ failure.

Numerous classes of drugs are used to treat Type 2 diabetes, including GLP-1 receptor agonists, such as exenatide (commercially available as BYETTA® from Amylin Pharmaceuticals, Inc. and Eli Lilly and Company). Despite the increased risk of pancreatitis in diabetic patients, the FDA issued an alert in October 2007 of a suspected association between BYETTA® and acute pancreatitis following a review of thirty post-marketing reports of acute pancreatitis in type 2 diabetic patients taking BYETTA®. In view of this FDA alert, studies were undertaken to determine what relationship, if any, existed between pancreatitis and GLP-1 receptor agonist compounds, such as exenatide.

The disclosure is directed to the findings that GLP-1 receptor agonists do not cause pancreatitis, but can actually be useful to treat pancreatitis.

SUMMARY

The disclosure provides methods for treating pancreatitis in humans by administering a therapeutically effective amount of exenatide to treat pancreatitis. In one embodiment, the pancreatitis is acute pancreatitis. In one embodiment, the pancreatitis is chronic pancreatitis. In other embodiments, the pancreatitis may be hemorrhagic pancreatitis, necrotizing pancreatitis, or hemorrhagic-necrotizing pancreatitis.

The disclosure provides methods for treating pancreatitis in patients by administering a therapeutically effective amount of a GLP-1 receptor agonist to treat pancreatitis. In one embodiment, the pancreatitis is acute pancreatitis. The pancreatitis may be acute pancreatitis, chronic pancreatitis, hemorrhagic pancreatitis, necrotizing pancreatitis, or hemorrhagic-necrotizing pancreatitis. Any GLP-1 receptor agonist compound may be used in the methods described herein. Exemplary GLP-1 receptor agonists include exenatide, lixisenatide, liraglutide, dulaglutide, albiglutide, and taspoglutide.

The disclosure provides methods for treating one or more symptoms of pancreatitis in patients by administering a therapeutically effective amount of a GLP-1 receptor agonist to treat one or more symptoms of pancreatitis. The symptoms of pancreatitis may be abdominal pain, back pain, swollen abdomen, nausea, vomiting, fever, rapid pulse, or a combination of two or more thereof. Any GLP-1 receptor agonist compound may be used in the methods described herein. Exemplary GLP-1 receptor agonists include exenatide, lixisenatide, liraglutide, dulaglutide, albiglutide, and taspoglutide.

The disclosure provides methods for treating diabetes in patients by administering a therapeutically effective amount of a GLP-1 receptor agonist to treat diabetes; identifying symptoms of pancreatitis or diagnosing pancreatitis in the patient; and continuing to administer the GLP-1 receptor agonist to the patient to treat diabetes. Any GLP-1 receptor agonist compound may be used in the methods described herein. Exemplary GLP-1 receptor agonists include exenatide, lixisenatide, liraglutide, dulaglutide, albiglutide, and taspoglutide.

The disclosure provides methods for treating diabetes and pancreatitis in patients by administering a therapeutically effective amount of a GLP-1 receptor agonist to treat diabetes; identifying symptoms of pancreatitis or diagnosing pancreatitis in the patient; and continuing to administer the GLP-1 receptor agonist to the patient to treat diabetes and pancreatitis. Any GLP-1 receptor agonist compound may be used in the methods described herein. Exemplary GLP-1 receptor agonists include exenatide, lixisenatide, liraglutide, dulaglutide, albiglutide, and taspoglutide.

The disclosure provides methods for treating diabetes in patients by advising patients of the symptoms of pancreatitis; administering to the patient a therapeutically effective amount of a GLP-1 receptor agonist to treat diabetes; identifying symptoms of pancreatitis or diagnosing pancreatitis in the patient; and continuing to administer the GLP-1 receptor agonist to treat diabetes and pancreatitis in the patient. The symptoms of pancreatitis may be abdominal pain, back pain, swollen abdomen, nausea, vomiting, fever, rapid pulse, or a combination of two or more thereof. Any GLP-1 receptor agonist compound may be used in the methods described herein. Exemplary GLP-1 receptor agonists include exenatide, lixisenatide, liraglutide, dulaglutide, albiglutide, and taspoglutide.

The disclosure provides methods to decrease the incidence and/or severity of pancreatitis-associated histopathological changes in the pancreas of patients by administering a therapeutically effective amount of a GLP-1 receptor agonist to decrease the incidence and/or severity of pancreatitis-associated histopathological changes in the pancreas. Any GLP-1 receptor agonist compound may be used in the methods described herein. Exemplary GLP-1 receptor agonists include exenatide, lixisenatide, liraglutide, dulaglutide, albiglutide, and taspoglutide.

The disclosure provides methods to decrease acute inflammation, vacuolation, neutrophilic infiltration, edema, necrosis, or a combination of two or more thereof in the pancreas of patients by administering a therapeutically effective amount of a GLP-1 receptor agonist to decrease acute inflammation, vacuolation, neutrophilic infiltration, edema, necrosis, or a combination of two or more thereof The vacuolation may be acinar cell vacuolation. The necrosis may be acinar cell necrosis. Any GLP-1 receptor agonist compound may be used in the methods described herein. Exemplary GLP-1 receptor agonists include exenatide, lixisenatide, liraglutide, dulaglutide, albiglutide, and taspoglutide.

The disclosure provides methods to reduce (i) plasma amylase concentration, (ii) plasma lipase concentration, or (iii) plasma amylase and plasma lipase concentrations in patients by administering a therapeutically effective amount of a GLP-1 receptor agonist to reduce the plasma amylase concentration, the plasma lipase concentration, or the plasma amylase and plasma lipase concentrations, respectively. Any GLP-1 receptor agonist compound may be used in the methods described herein. Exemplary GLP-1 receptor agonists include exenatide, lixisenatide, liraglutide, dulaglutide, albiglutide, and taspoglutide.

DETAILED DESCRIPTION

Figure 1:
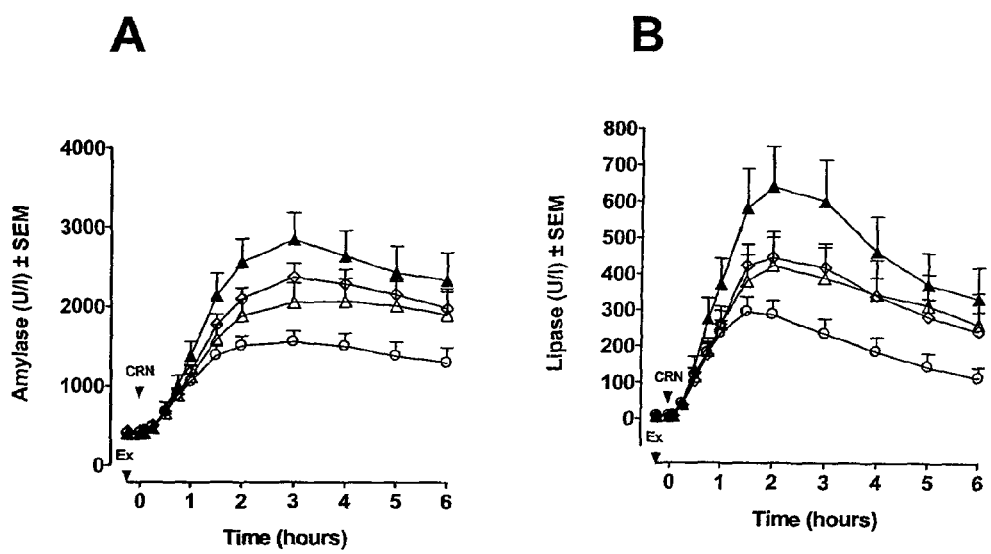
FIGS. 1A-B: Time course of plasma amylase (FIG. 1A) and lipase (FIG. 1B) in normal HSD rats that received a single s.c. dose of exenatide ((0.072 (open diamonds), 0.24 (open triangles), 0.72 nmol/kg (open circles)) or vehicle (black triangles). Pancreatitis was induced with a single dose of caerulein.

Type 2 diabetes is a risk factor for developing pancreatitis. Type 2 diabetic patients treated with GLP-1 receptor agonist compounds have developed pancreatitis. To understand what role (if any) that GLP-1 receptor agonists may play in pancreatitis, an evaluation was undertaken to determine the effects of a GLP-1 receptor agonist (i.e., exenatide) on rodent models with and without chemically-induced pancreatitis. The disclosure is based on the unexpected finding that GLP-1 receptor agonists, such as exenatide, are useful in treating pancreatitis in patients, such as those patients with Type 2 diabetes.

The disclosure provides methods of treating pancreatitis in a patient in need thereof by administering a therapeutically effective amount of a GLP-1 receptor agonist to the patient to treat pancreatitis. The pancreatitis may be acute pancreatitis, hemorrhagic pancreatitis (e.g., acute hemorrhagic pancreatitis), necrotizing pancreatitis (e.g., acute necrotizing pancreatitis), hemorrhagic-necrotizing pancreatitis (e.g., acute hemorrhagic-necrotizing pancreatitis), or chronic pancreatitis. The GLP-1 receptor agonist may be any known in the art, such as those described herein.

The disclosure provides methods of treating one or more symptoms of pancreatitis in a patient in need thereof by administering a therapeutically effective amount of a GLP-1 receptor agonist to the patient to treat one or more symptoms of pancreatitis. Exemplary symptoms of pancreatitis include abdominal pain, back pain, swollen abdomen, nausea, vomiting, fever, rapid pulse, and the like. The GLP-1 receptor agonist may be any known in the art, such as those described herein.

The disclosure provides methods to reduce elevated plasma amylase concentrations in a patient in need thereof by administering a therapeutically effective amount of a GLP-1 receptor agonist compound to the patient to reduce the elevated plasma amylase concentrations. The patient may have a plasma amylase concentration that is elevated above normal (e.g., elevated above 200 U/L). The disclosure provides methods to reduce elevated plasma lipase concentrations in a patient in need thereof by administering a therapeutically effective amount of a GLP-1 receptor agonist compound to the patient to reduce the elevated plasma lipase concentrations. The patient may have a plasma lipase concentration that is elevated above normal (e.g., elevated above 150 U/L). The disclosure provides methods to reduce plasma amylase concentrations and plasma lipase concentrations in a patient in need thereof by administering a therapeutically effective amount of a GLP-1 receptor agonist compound to the patient to reduce the plasma amylase and plasma lipase concentrations. The GLP-1 receptor agonist may be any known in the art, such as those described herein.

The disclosure provides methods to decrease the incidence and/or severity of histopathological changes in the pancreas of a patient in need thereof by administering a therapeutically effective amount of a GLP-1 receptor agonist compound to the patient to decrease the incidence and/or severity of the histopathological changes in the pancreas. The disclosure provides methods to decrease acute inflammation, vacuolation (e.g., acinar cell vacuolation), neutrophilic infiltration, edema, necrosis (e.g., acinar cell necrosis), or a combination of two or more thereof in the pancreas of patients in need thereof by administering a therapeutically effective amount of a GLP-1 receptor agonist compound to a patient in need thereof. The GLP-1 receptor agonist may be any known in the art, such as those described herein.

The disclosure provides methods for treating diabetes in a patient in need thereof by administering a therapeutically effective amount of a GLP-1 receptor agonist compound to treat diabetes in the patient; identifying symptoms of pancreatitis or diagnosing pancreatitis in the patient; and continuing to administer the GLP-1 receptor agonist compound to treat diabetes and pancreatitis in the patient. The method further involves continuing to administer the GLP-1 receptor agonist compound to treat diabetes after the patient recovers from the pancreatitis. The GLP-1 receptor agonist may be any known in the art, such as those described herein.

The disclosure provides methods for treating diabetes in a patient in need thereof by advising a patient of the symptoms of pancreatitis; administering a therapeutically effective amount of a GLP-1 receptor agonist compound to treat diabetes in the patient; identifying symptoms of pancreatitis or diagnosing pancreatitis in the patient; and continuing to administer the GLP-1 receptor agonist compound to treat diabetes and pancreatitis in the patient. The method further involves continuing to administer the GLP-1 receptor agonist compound to treat diabetes after the patient recovers from the pancreatitis.

The term "diabetes" refers to Type 1 diabetes, Type 2 diabetes, and gestational diabetes; preferably Type 2 diabetes.

The term "patient" refers to mammals, preferably humans. In some embodiments, the patient is a human. In some embodiments, the patient is a human with Type 2 diabetes or an obese human with Type 2 diabetes.

A "GLP-1 receptor agonist" refers to compounds having GLP-1 receptor activity. Such exemplary compounds include exendins, exendin analogs, exendin agonists, GLP-1(7-37), GLP-1(7-37) analogs, GLP-1(7-37) agonists, and the like. The GLP-1 receptor agonist compounds may optionally be amidated. The terms "GLP-1 receptor agonist" and "GLP-1 receptor agonist compound" have the same meaning.

The term "exendin" includes naturally occurring (or synthetic versions of naturally occurring) exendin peptides that are found in the salivary secretions of the Gila monster. Exendins of particular interest include exendin-3 and exendin-4. The exendins, exendin analogs, and exendin agonists for use in the methods described herein may optionally be amidated, and may also be in an acid form, pharmaceutically acceptable salt form, or any other physiologically active form of the molecule.

Exendin-4 (HGEGTFTSDLSKQMEEEAVR-LFIEWLKNGGPSSGAPPPS-NH$_2$ (SEQ ID NO:1)) is a peptide found in the saliva of the Gila monster, *Heloderma suspectum*; and exendin-3 (HSDGTFTSDLSKQMEEEAVRLFIEWLKNGG PSS-GAPPPS-NH$_2$ (SEQ ID NO:2)) is a peptide found in the saliva of the beaded lizard, *Heloderma horridum*. Exendins have some amino acid sequence similarity to some members of the glucagon-like peptide (GLP) family. For example, exendin-4 has about 53% sequence identity with glucagon-like peptide-1(GLP-1)(7-37) (HAEGTFTSDVS-SYLEGQAAKEFIAWLVKGRG (SEQ ID NO:22)). However, exendin-4 is transcribed from a distinct gene, not the Gila monster homolog of the mammalian proglucagon gene from which GLP-1 is expressed. Additionally, exendin-4 is not an analog of GLP-1(7-37) because the structure of synthetic exendin-4 peptide was not created by sequential modification of the structure of GLP-1. Nielsen et al., *Current Opinion in Investigational Drugs*, 4(4):401-405 (2003).

Synthetic exendin-4, also known as exenatide, is commercially available as BYETTA® (Amylin Pharmaceuticals, Inc. and Eli Lilly and Company). A once weekly formulation of exenatide is described in WO 2005/102293, the disclosure of which is incorporated by reference herein.

"Exendin analog" refers to peptides which elicit a biological activity of an exendin reference peptide, preferably having a potency equal to or better than the exendin reference peptide (e.g., exendin-4), or within five orders of magnitude (plus or minus) of potency compared to the exendin reference peptide, when evaluated by art-known measures such as receptor binding and/or competition studies as described, e.g., by Hargrove et al., *Regulatory Peptides*, 141:113-119 (2007), the disclosure of which is incorporated by reference herein. Preferably, the exendin analogs will bind in such assays with an affinity of less than 1 µM, and more preferably with an affinity of less than 3 nM, less than 1 nM, or less than 0.1 nM. The term "exendin analog" may also be referred to as "exendin agonist". In a preferred embodiment, the exendin analog is an exendin-4 analog.

Exendin analogs also include the peptides described herein which have been chemically derivatized or altered, for example, peptides with non-natural amino acid residues (e.g., taurine, β-amino acid residues, γ-amino acid residues, and D-amino acid residues), C-terminal functional group modifications, such as amides, esters, and C-terminal ketone modifications and N-terminal functional group modifications, such as acylated amines, Schiff bases, or cyclization, as found, for example, in the amino acid pyroglutamic acid. Exendin analogs may also contain other chemical moieties, such as peptide mimetics.

Exemplary exendins and exendin analogs exendin-4 (SEQ ID NO:1); exendin-3 (SEQ ID NO:2); Leu$^{14}$-exendin-4 (SEQ ID NO:3); Leu$^{14}$,Phe$^{25}$-exendin-4 (SEQ ID NO:4); Leu$^{14}$, Ala$^{19}$,Phe$^{25}$-exendin-4 (SEQ ID NO:5); exendin-4(1-30) (SEQ ID NO:6); Leu$^{14}$-exendin-4(1-30) (SEQ ID NO:7); Leu$^{14}$,Phe$^{25}$-exendin-4(1-30) (SEQ ID NO:8); Leu$^{14}$,Ala$^{19}$, Phe$^{25}$-exendin-4(1-30) (SEQ ID NO:9); exendin-4(1-28) (SEQ ID NO:10); Leu$^{14}$-exendin-4(1-28) (SEQ ID NO:11); Leu$^{14}$,Phe$^{25}$-exendin-4(1-28) (SEQ ID NO:12); Leu$^{14}$,Ala$^{19}$, Phe$^{25}$-exendin-4 (1-28) (SEQ ID NO:13); Leu$^{14}$,Lys$^{17,20}$, Ala$^{19}$,Glu$^{21}$,Phe$^{25}$,Gln$^{28}$-exendin-4 (SEQ ID NO:14); Leu$^{14}$, Lys$^{17,20}$,Ala$^{19}$,Glu$^{21}$,Gln$^{28}$-exendin-4 (SEQ ID NO:15); octylGly$^{14}$,Gln$^{28}$-exendin-4 (SEQ ID NO:16); Leu$^{14}$,Gln$^{28}$, octylGly$^{34}$-exendin-4 (SEQ ID NO:17); Phe$^{4}$,Leu$^{14}$,Gln$^{28}$, Lys$^{33}$,Glu$^{34}$, Ile$^{35,36}$,Ser$^{37}$-exendin-4(1-37) (SEQ ID NO:18); Phe$^{4}$,Leu$^{14}$,Lys$^{17,20}$,Ala$^{19}$,Glu$^{21}$,Gln$^{28}$-exendin-4 (SEQ ID NO:19); Val$^{11}$,Ile$^{13}$,Leu$^{14}$,Ala$^{16}$,Lys$^{21}$,Phe$^{25}$-exendin-4 (SEQ ID NO:20); exendin-4-Lys$^{40}$ (SEQ ID NO:21); lixisenatide (Sanofi-Aventis/Zealand Pharma); CJC-1134 (ConjuChem, Inc.); [N$^e$-(17-carboxyheptadecanoic acid) Lys$^{20}$]exendin-4-NH$_2$ (SEQ ID NO: 46); [N$^e$-(17-carboxy-hepta-decanoyl)Lys$^{32}$]exendin-4-NH$_2$ (SEQ ID NO: 47); [desamino-His$^{1}$,N$^e$-(17-carboxyheptadecanoyl)Lys$^{20}$]exendin-4-NH$_2$ (SEQ ID NO: 48); [Arg$^{12,27}$,NLe$^{14}$,N$^e$-(17-carboxy-heptadecanoyl)Lys$^{32}$]exendin-4-NH$_2$ (SEQ ID NO: 49); [N$^e$-(19-carboxy-nonadecanoylamino)Lys$^{20}$]-exendin-4-NH$_2$ (SEQ ID NO: 50); [N$^e$-(15-carboxypentadecanoylamino)Lys$^{20}$]-exendin-4-NH$_2$ (SEQ ID NO: 51); [N$^e$-(13-carboxytridecanoylamino)Lys$^{20}$]exendin-4-NH$_2$ (SEQ ID NO: 52); [N$^e$-(11-carboxy-undecanoyl-amino)Lys$^{20}$]exendin-4-NH$_2$ (SEQ ID NO: 53); exendin-4-Lys$^{40}$(e-MPA)-NH$_2$ (SEQ ID NO: 54); exendin-4-Lys$^{40}$(e-AEEA-AEEA-MPA)-NH$_2$ (SEQ ID NO: 55); exendin-4-Lys$^{40}$(e-AEEA-MPA)-NH$_2$ (SEQ ID NO: 56); exendin-4-Lys$^{40}$(e-MPA)-albumin (SEQ ID NO: 57); exendin-4-Lys$^{40}$(e-AEEA-AEEA-MPA)-albumin (SEQ ID NO: 58); exendin-4-Lys$^{40}$(e-AEEA-MPA)-albumin (SEQ ID NO: 59); and the like. AEEA refers to [2-(2-amino)ethoxy)]acetic acid. EDA refers to ethylenediamine. MPA refers to maleimidopropionic acid. The exendins and exendin analogs may optionally be amidated.

In one embodiment, the GLP-1 receptor agonist compound is an exendin-4 analog that has at least 80% sequence identity to exendin-4 (SEQ ID NO:1); at least 85% sequence identity to exendin-4 (SEQ ID NO:1); at least 90% sequence identity to exendin-4 (SEQ ID NO:1); or at least 95% sequence identity to exendin-4 (SEQ ID NO:1).

Other exendins and exendin analogs useful in the methods described herein include those described in WO 98/05351; WO 99/07404; WO 99/25727; WO 99/25728; WO 99/40788; WO 00/41546; WO 00/41548; WO 00/73331; WO 01/51078; WO 03/099314; U.S. Pat. No. 6,956,026; U.S. Pat. No. 6,506,724; U.S. Pat. No. 6,703,359; U.S. Pat. No. 6,858,576; U.S. Pat. No. 6,872,700; U.S. Pat. No. 6,902,744; U.S. Pat. No. 7,157,555; U.S. Pat. No. 7,223,725; U.S. Pat. No. 7,220,721; US Publication No. 2003/0036504; and US Publication No. 2006/0094652, the disclosures of which are incorporated by reference herein in their entirety.

"GLP-1(7-37) analogs" refers to peptides which elicit a biological activity similar to that of GLP-1(7-37), when evaluated by art-known measures such as receptor binding assays or in vivo blood glucose assays as described, e.g., by Hargrove et al., *Regulatory Peptides*, 141:113-119 (2007), the disclosure of which is incorporated by reference herein. In one embodiment, the term "GLP-1(7-37) analog" refers to a peptide that has an amino acid sequence with 1, 2, 3, 4, 5, 6, 7 or 8 amino acid substitutions, insertions, deletions, or a combination of two or more thereof, when compared to the amino acid sequence of GLP-1(7-37). In one embodiment, the GLP-1(7-37) analog is GLP-1(7-36)-NH$_2$. GLP-1(7-37) analogs include the amidated forms, the acid form, the pharmaceutically acceptable salt form, and any other physiologically active form of the molecule.

Exemplary GLP-1(7-37) and GLP-1(7-37) analogs include GLP-1(7-37) (SEQ ID NO:22); GLP-1(7-36)-NH$_2$ (SEQ ID NO:23); liraglutide (VICTOZA® from Novo Nordisk); albiglutide (SYNCRIA® from GlaxoSmithKline); tas-poglutide (Hoffman La-Roche); dulaglutide (also known LY2189265; Eli Lilly and Company); LY2428757 (Eli Lilly and Company); desamino-His$^7$,Arg$^{26}$,Lys$^{34}$(N$^\epsilon$-(γ-Glu(N-α-hexadecanoyl)))-GLP-1(7-37) (core peptide disclosed as SEQ ID NO: 60); desamino-His$^7$,Arg$^{26}$,Lys$^{34}$(N$^\epsilon$-octanoyl)-GLP-1(7-37) (SEQ ID NO: 61); Arg$^{26,34}$,Lys$^{38}$(N$^\epsilon$-(ω-carboxypentadecanoyl))-GLP-1(7-38) (SEQ ID NO: Arg$^{26,34}$, Lys$^{36}$(N$^\epsilon$-(γ-Glu(N-α-hexadecanoyl)))-GLP-1(7-36) (core peptide disclosed as SEQ ID NO: 63); Aib$^{8,35}$,Arg$^{26,34}$, Phe$^{31}$-GLP-1(7-36)) (SEQ ID NO:24); HXaa$_8$EGTFTSDVSSYLEXaa$_{22}$Xaa$_{23}$AAKEFIXaa$_{30}$W-LXaa$_{33}$Xaa$_{34}$G Xaa$_{36}$Xaa$_{37}$; wherein Xaa$_3$ is A, V, or G; Xaa$_{22}$ is G, K, or E; Xaa$_{23}$ is Q or K; Xaa$_{30}$ is A or E; Xaa$_{33}$ is V or K; Xaa$_{34}$ is K, N, or R; Xaa$_{36}$ is R or G; and Xaa$_{37}$ is G, H, P, or absent (SEQ ID NO:25); Arg$^{34}$-GLP-1(7-37) (SEQ ID NO:26); Glu$^{30}$-GLP-1(7-37) (SEQ ID NO:27); Lys$^{22}$-GLP-1(7-37) (SEQ ID NO:28); Gly$^{8,36}$,Glu$^{22}$-GLP-1(7-37) (SEQ ID NO:29); Val$^8$,Glu$^{22}$,Gly$^{36}$-GLP-1(7-37) (SEQ ID NO:30); Gly$^{8,36}$,Glu$^{22}$,Lys$^{33}$,Asn$^{34}$-GLP-1(7-37) (SEQ ID NO:31); Val$^8$,Glu$^{22}$,Lys$^{33}$,Asn$^{34}$,Gly$^{36}$-GLP-1(7-37) (SEQ ID NO:32); Gly$^{8,36}$,Glu$^{22}$,Pro$^{37}$-GLP-1(7-37) (SEQ ID NO:33); Val$^8$,Glu$^{22}$,Gly$^{36}$Pro$^{37}$-GLP-1(7-37) (SEQ ID NO:34); Gly$^{8,36}$,Glu$^{22}$,Lys$^{33}$, Asn$^{34}$,Pro$^{37}$-GLP-1(7-37) (SEQ ID NO:35); Val$^8$,Glu$^{22}$,Lys$^{33}$,Asn$^{34}$,Gly$^{36}$,Pro$^{37}$-GLP-1(7-37) (SEQ ID NO:36); Gly$^{8,36}$,Glu$^{22}$-GLP-1(7-36) (SEQ ID NO:37); Val$^8$,Glu$^{22}$,Gly$^{36}$-GLP-1(7-36) (SEQ ID NO:38); Val$^8$,Glu$^{22}$,Asn$^{34}$,Gly$^{36}$-GLP-1(7-36) (SEQ ID NO:39); Gly$^{8,36}$,Glu$^{22}$,Asn$^{34}$-GLP-1(7-36) (SEQ ID NO:40). Each of the GLP-1(7-37) and GLP-1(7-37) analogs may optionally be amidated.

In one embodiment, the GLP-1(7-37) or GLP-1(7-37) analogs are covalently linked (directly or by a linking group) to an Fc portion of an immunoglobulin (e.g., IgG, IgE, IgG, and the like). For example, any one of SEQ ID NOs:25-40 may be covalently linked to the Fc portion of an immunoglobulin comprising the sequence of: AESKYGPPCPPCPAPXaa$_{16}$Xaa$_{17}$Xaa$_{18}$GGPSVFLFPPKPKDTLMISRTPEVTCVVV-DVSQEDPEVQFNWYVDGVEVH NAKTKPREEQFXaa$_{80}$S-TYRVVSVLTVLHQDWLNGKEYKCK-VSNKGLPSSIEKTISKAKG QPREPQVYTLPPSQEEMT-KNQVSLTCLVKGFYPSDIA-VEWESNGQPENNYKTTPPVLD SDGSFFLYSRLTVDKSRWQEGNVFSCS-VMHEALHNHYTQKSLSLSLGXaa$_{230}$; wherein Xaa$_{16}$ is P or E; Xaa$_{17}$ is F, V or A; Xaa$_{18}$ is L, E or A; Xaa$_{80}$ is N or A; and Xaa$_{230}$ is K or absent (SEQ ID NO:41). The linking group may be any chemical moiety (e.g., amino acids and/or chemical groups). In one embodiment, the linking group is (-GGGGS-)$_x$ (SEQ ID NO:42) where x is 1, 2, 3, 4, 5 or 6; preferably 2, 3 or 4; more preferably 3. In one embodiment, the GLP-1(7-37) analog covalently linked to the Fc portion of an immunoglobulin comprises the amino acid sequence: HGEGTFTSDVSSYLEEQAAKEFIAWLVK GGGGGGGSGGGGSGGGGSAE SKYGPPCPPCPA-PEAAGGPSVFLFPPK PKDTLMISRTPEVTCVVVD-VSQEDPE VQFNWYVDGVEVHNAKTKPREEQFN-STYR VVSVLTVLHQDWLNGKEYKCK VSNKGLPSSIEKTISKAKGQPREPQVYTL PPSQEEMT-KNQVSLTCLVKGFYPSDI AVEWESNGQPENNYKTTP-PVLDSDGSFFLYSR LTVDKSRWQEGNVFSCSVMHEA LHNHYTQ KSLSLSLG (SEQ ID NO:43).

In another embodiment, the GLP-1(7-37) or GLP-1(7-37) analog may be covalently linked (directly or through a linking group) to one or two polyethylene glycol molecules. For example, a GLP-1(7-37) analog may comprise the amino acid sequence: HXaa$_8$EGTFTSDVS SYLEXaa$_{22}$QA-AKEFIAWLXaa$_{33}$KGGPSSGAPPPC$_{45}$C$_{46}$-Z, wherein Xaa$_8$ is: D-Ala, G, V, L, I, S or T; Xaa$_{22}$ is G, E, D or K; Xaa$_{33}$ is: V or I; and Z is OH or NH$_2$, (SEQ ID NO:44), and, optionally, wherein (i) one polyethylene glycol moiety is covalently attached to C$_{45}$, (ii) one polyethylene glycol moiety is covalently attached to C$_{46}$, or (iii) one polyethylene glycol moiety is attached to C$_{45}$ and one polyethylene glycol moiety is attached to C$_{46}$. In one embodiment, the GLP-1(7-37) analog is HVEGTFTSDVSSYLEEQAAKEFI AWLIKGGPSSGAPPPC$_{45}$C$_{46}$-NH$_2$ (SEQ ID NO:45) and, optionally, wherein (i) one polyethylene glycol moiety is covalently attached to C$_4$, (ii) one polyethylene glycol moiety is covalently attached to C$_{46}$, or (iii) one polyethylene glycol moiety is attached to C$_{45}$ and one polyethylene glycol moiety is attached to C$_{46}$.

In one embodiment, the GLP-1 receptor agonist compound is a peptide that has at least 80% sequence identity to GLP-1(7-37) (SEQ ID NO:22); at least 85% sequence identity to GLP-1(7-37) (SEQ ID NO:22); at least 90% sequence identity to GLP-1(7-37) (SEQ ID NO:22); or at least 95% sequence identity to GLP-1(7-37) (SEQ ID NO:22).

GLP-1 receptor agonist compounds may be prepared by processes well known in the art, e.g., peptide purification as described in Eng et al., *J. Biol. Chem.*, 265:20259-62 (1990); standard solid-phase peptide synthesis techniques as described in Raufman et al., *J. Biol. Chem.*, 267:21432-37 (1992); recombinant DNA techniques as described in Sambrook et al., *Molecular Cloning: A Laboratory Manual*, 2d Ed., Cold Spring Harbor (1989); and the like.

The disclosure also provides pharmaceutical compositions comprising the GLP-1 receptor agonist compounds described herein and a pharmaceutically acceptable carrier. The GLP-1 receptor agonist compounds can be present in the pharmaceutical composition in a therapeutically effective amount and can be present in an amount to provide a minimum blood plasma level of the GLP-1 receptor agonist compound necessary for therapeutic efficacy. Such pharmaceutical compositions are known in the art and described, e.g., in U.S. Pat. No. 7,521,423; U.S. Pat. No. 7,456,254; WO 2000/037098; WO 2005/021022; WO 2005/102293; WO 2006/068910; WO 2006/125763; WO 2009/068910; US Publication No. 2004/0106547; and the like, the disclosures of which are incorporated herein by reference.

Pharmaceutical compositions containing the GLP-1 receptor agonist compounds described herein may be provided for peripheral administration, such as parenteral (e.g., subcutaneous, intravenous, intramuscular), a continuous infusion (e.g., intravenous drip, intravenous bolus, intravenous infusion), topical, nasal, or oral administration. Suitable pharmaceutically acceptable carriers and their formulation are described in standard formulation treatises, such as Remington's Pharmaceutical Sciences by Martin; and Wang et al., *Journal of Parenteral Science and Technology*, Technical Report No. 10, Supp. 42:2S (1988). The GLP-1 receptor agonist compounds described herein can be provided in parenteral compositions for injection or infusion. They can, for example, be suspended in water; an inert oil, such as a vegetable oil (e.g., sesame, peanut, olive oil, and the like); or other pharmaceutically acceptable carrier. In one embodiment, the compounds are suspended in an aqueous carrier, for example, in an isotonic buffer solution at a pH of about 3.0 to 8.0, or about 3.0 to 5.0. The compositions may be sterilized by conventional sterilization techniques or may be sterile filtered. The compositions may contain pharmaceutically acceptable auxiliary substances as required to approximate physiological conditions, such as pH buffering agents.

Useful buffers include for example, acetic acid buffers. A form of repository or "depot" slow release preparation may be used so that therapeutically effective amounts of the preparation are delivered into the bloodstream over many hours or days following subcutaneous injection, transdermal injection or other delivery method. The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. In one embodiment for intravenous infusion, the formulation may comprise (i) the GLP-1 receptor agonist compound, (2) sterile water, and, optionally (3) sodium chloride, dextrose, or a combination thereof.

Carriers or excipients can also be used to facilitate administration of the GLP-1 receptor agonist compounds. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents.

The GLP-1 receptor agonist compounds can also be formulated as pharmaceutically acceptable salts (e.g., acid addition salts) and/or complexes thereof. Pharmaceutically acceptable salts are non-toxic salts at the concentration at which they are administered. Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Exemplary pharmaceutical formulations of GLP-1 receptor agonist compounds are described in U.S. Pat. No. 7,521,423, U.S. Pat. No. 7,456,254; US Publication No 2004/0106547, WO 2006/068910, WO 2006/125763, and the like, the disclosures of which are incorporated by reference herein.

The therapeutically effective amount of the GLP-1 receptor agonist compounds described herein for use in the methods described herein will typically be from about 0.01 µg to about 5 mg; about 0.1 µg to about 2.5 mg; about 1 µg to about 1 mg; about 1 µg to about 50 µg; or about 1 µg to about 25 µg. Alternatively, the therapeutically effective amount of the GLP-1 receptor agonist compounds may be from about 0.001 µg to about 100 µg based on the weight of a 70 kg patient; or from about 0.01 µg to about 50 µg based on the weight of a 70 kg patient. These therapeutically effective doses may be administered once/day, twice/day, thrice/day, once/week, biweekly, or once/month, depending on the formulation. The exact dose to be administered is determined, for example, by the formulation, such as an immediate release formulation or an extended release formulation. For transdermal, nasal or oral dosage forms, the dosage may be increased from about 5-fold to about 10-fold.

EXAMPLES

To understand what role (if any) that GLP-1 receptor agonists would have in pancreatitis, the effects of exenatide on rodent models with and without chemically-induced acute pancreatitis were evaluated as described herein.

Example 1

This Example is also described in Tatarkiewicz et al., "Exenatide does not evoke pancreatitis and attenuates chemically induced pancreatitis in normal and diabetic rodents," *Am J Physiol Endocrinol Metab*, E1076-E1086 (October 2010), the disclosure of which is incorporated herein by reference.

Methods: Normal HSD or Wistar rats and diabetic ZDF rats received a single dose of exenatide (0.072 nmol/kg, 0.24 nmol/kg, 0.72 nmol/kg) or vehicle. Diabetic ob/ob or HF-STZ mice were dosed with exenatide (1.2 nmol/kg/d, 7.2 nmol/kg/d) or vehicle by continuous infusion for 4 weeks. Pancreatitis was induced with caerulein or sodium taurocholate (ST) after administration of exenatide. Amylase and lipase plasma levels were measured at different time points. Plasma cytokines (Il-1 β, Il-2, Il-6, MCP-1, IFN-γ, and TNF-α) were assessed in ob/ob mice. Pancreata were weighted at the end of each study. Analyses of expression of pancreatitis-associated genes and histology were performed on pancreata.

Results: Pretreatment with exenatide did not modify baseline amylase and lipase levels in acute or chronic studies of animals without pancreatitis. Exenatide attenuated caerulein-induced mild pancreatitis in HSD rats and ob/ob mice demonstrated by decreased amylase and lipase in comparison to vehicle-treated control groups. sodium taurocholate infusion in rats resulted in a severe acute pancreatitis and exenatide did not modify the pancreatic enzyme response to this injury. A trend towards attenuation of IL-6, MCP-1 and TNF-α responses to caerulein was observed with exenatide treatment. Pancreatic weight was not affected by treatment with exenatide in any of the studies. Exenatide upregulated Reg3b gene expression and did not modify Il6, Ccl2, Nfkb1 or Vamp8 gene expression. Histological analysis revealed that exenatide decreased caerulein- or sodium taurocholate-induced acute inflammation, vacuolation and acinar single cell necrosis in mice and rats, respectively. Duct cell proliferation rate was low (<1%) and similar across all groups of ob/ob mice including wild type controls.

Generation of high-fat fed and streptozotocin-induced diabetic mouse model: C57BL/6 mice, maintained on a high fat diet at Jackson Laboratories starting at 4 weeks of age through 10 weeks of age. To induce experimental diabetes, animals were dosed intraperitoneally (i.p.) with streptozotocin (100 mg/kg) once weekly for 2 consecutive weeks. Controls (non-diabetic) received 0.1 M citrate buffer as vehicle at the same intervals as the streptozotocin groups. At 14 weeks of age, diabetic animals were randomized into treatment groups based on HbAlc.

Induction of experimental pancreatitis: The CCK receptor agonist caerulein (Sigma-Aldrich) was used to induce acute pancreatitis in fasted animals, which were treated acutely or sub-chronically with exenatide as described below. Caerulein was reconstituted in commercially available 0.9% saline and administered by five consecutive hourly i.p. injections at 10 µg/kg in mice or by single i.p. injection (10 µg/kg in rats). Control animals received only saline injections. The doses of caerulein were selected to induce low levels of pancreatic tissue damage and inflammation. More severe acute insult to the pancreas was made in anesthetized Wistar rats through transduodenal cannulation of the biliopancreatic duct followed by retrograde infusion of 5% sodium taurocholate at a rate of 0.05 ml/min using an infusion pump (Model #2400-006, Harvard Apparatus). Animals received a total volume of 1 ml/kg body weight. Sham surgery consisted of laparotomy, duodenal incision and closure.

Administration of exenatide: To assess the effects of acute pretreatment with exenatide on caerulein-induced pancreatitis, exenatide was administered as a single i.p. dose (1.2 and 7.2 nmol/kg) in mice or a single s.c. dose (0.072, 0.24, 0.72 nmol/kg) in anesthetized rats 15 minutes prior to caerulein insult. The same doses of exenatide were administered twice a day for 48 hours in rats with sodium taurocholate-induced pancreatitis with the first injection applied 15 minutes before the sodium taurocholate infusion. In the sub-chronic studies in mice, exenatide was administered at 1.2 and 7.2 nmol/kg/day via continuous subcutaneous infusion for 4 weeks. The peptide was reconstituted in 50% DMSO in sterile water supplemented with 0.1% bovine serum albumin and loaded into ALZET® ((Model 2002), Cupertino, Calif.) osmotic 2-week mini-pumps according to the manufacturer's protocol. After 14 days, mice were re-implanted with new mini-pumps administering the same treatments for the next 2 weeks. Control groups received mini-pumps loaded with vehicle as described above.

Biochemical analysis: At various time points, blood samples were collected into heparinized capillary tubes via the retro-orbital sinus from non-anesthetized mice. Terminal samples from isofluorane-anesthetized mice were collected by cardiac puncture. In the caerulein-induced pancreatitis model in anesthetized rats, blood samples, taken from the femoral artery, were collected into heparinized Natelson tubes. In sodium taurocholate-induced pancreatitis model, samples were collected into heparinized tubes from the tail vein of non-anesthetized rats. Terminal samples were collected from anesthetized animals via cardiac puncture. All samples were processed for plasma and stored at −80° C. for later analysis. Plasma amylase and lipase were measured using either the Olympus AU400e or AU680 clinical analyzer (Olympus America, Inc, Irving, Tex.) in accordance with the manufacturer's protocol. Plasma samples for interleukins: 1β(Il-1 β), 2 (Il-2), 6 (Il-6), and MCP-1, IFN-γ, TNF-α were collected from ob/ob mice at 6 hours post first caerulein injection. Cytokine concentrations were measured using the Milliplex Mouse Cytokine/Chemokine multiplexing immunoassay kit according to manufacturer protocol (Millipore, Billerica, Mass.). Median Flourescent Intensity (MFI) was determined using the Luminex instrument (Luminex, Austin, Tex.). Cytokine concentrations were calculated using 4-PL logistic method (SoftMax Pro, Molecular Devices, Sunnyvale, Calif.).

Histology and gene expression: Mouse and rat pancreata were dissected, weighed, immediately fixed in 10% neutral-buffered formalin and embedded in paraffin. Five-micron sections from specimens from each animal were stained for haematoxylin and eosin. Histopathological scoring analyses were performed by board-certified independent veterinary histopathologists, who were aware of group assignment.

To determine ductal cell replication Ki-67 and pan-cytokeratin were used as markers of proliferation and ductal cells, respectively. For immunofluorescence, pancreas sections were deparaffinized in SafeClear (Fisher, 23-314-629, Waltham, Mass.) and rehydrated in ethanol gradient. Antigen retrieval was performed via microwave heating in citrate-buffer (Dako, S2369, Carpinteria, Calif.) for 32 minutes. Slides were blocked in Avidin/Biotin Blocking Kit (Vector, SP2001, Burlingame, Calif.) and then Protein Block, Serum-Free, (Dako, X0909, Carpinteria, Calif.). The following primary antibodies were used: Ki67 (Rat anti-mouse, 1:25; Dako, M7249, Carpinteria, Calif.), cytokeratin (rabbit anti-mouse anti-pancytokeratin, 1:50; NC9726269, AbCam, Cambridge, Mass.). Secondary antibody labeled with FITC (1:50 for 1-hour incubation) was used for cytokeratin visualization (Millipore, AP187FMI, Temecula, Calif.). Secondary antibody for Ki-67 (Vector, biotinylated anti-rat, 1:300; A-2002, Burlingame, Calif.) was applied for 1-hour followed with the fluorophore Rhodamine Avidin D for 10 minutes (1:200; Vector, A-2002, Burlingame, Calif.). For quantification of ductal cell replication, cytokeratin positive cells (~1000 per section) were counted. The frequency of ductal cell replication in each animal was presented as a percentage of total number of Ki-67 positive ductal cells per total number of cytokeratin positive cells.

Expression of genes encoding inflammatory mediators (Il-6, MCP-1, Nf-κB, MPO), tissue regeneration (Reg3b, Egr-1, Icam-1) or exocytosis in acinar cells (VAMPS) were assessed in formalin fixed paraffin embedded mouse samples using the QuantiGene Plex 2.0 multiplexing assay (Affymetrix, Fremont, Calif.) according to manufacturer protocol. For normalization, Gapdh was used as housekeeping gene.

Statistical analyses: Results are graphed using Prism 4 (Graph Pad, San Diego, Calif.) and data are presented as mean±SEM. The areas under the curve (AUC) for amylase and lipase were calculated by trapezoid method. Statistical analyses were performed with Prism 4 or SAS 8.2 (SAS Institute, Inc., Cary, N.C.). Statistical differences between treatment groups ($p<0.05$) and appropriate controls were identified with one-way ANOVA followed with Dunnett's or Bonferroni's multiple comparison tests. For some endpoints, as indicated in Results section, measurements were $\log_{10}$-transformed to more fully comply with normality assumptions and ANOVA was performed on transformed data.

Effect of exenatide on baseline amylase and lipase release: Exenatide administered as a single injection to normal HSD or ZDF rats at doses ranging from 0.072 to 0.72 nmol/kg had no effect on plasma amylase or lipase through the duration of measurements (6 hours) when compared to vehicle control. Accordingly, calculated areas under the curve (AUC) for 0-6 h excursions of amylase or lipase did not differ from their respective vehicle controls in both strains of rats ($p>0.05$). However, levels of amylase or lipase in these animals were respectively approximately 1.5- and 2.5-fold higher than in normal rats. Similarly, exenatide had no effect on basal plasma amylase or lipase during sub-chronic (4 week) continuous subcutaneous dosing at 7.2 nmol/kg/d in diabetic ob/ob or HF-STZ mice. This dose of exenatide in both mouse studies significantly decreased HbAlc compared with the corresponding vehicle treated controls.

Acute effects of exenatide on amylase and lipase during chemically-induced pancreatitis: A single intraperitoneal dose of 10 µg/kg caerulein induced dramatic increases in plasma amylase and lipase in normal HSD and diabetic ZDF rats. Intraductal infusion of sodium taurocholate resulted in approximately 3-fold more amylase and lipase release than was stimulated with caerulein, indicating a greater severity of experimental pancreatitis than in the sodium taurocholate model.

Figure 2:
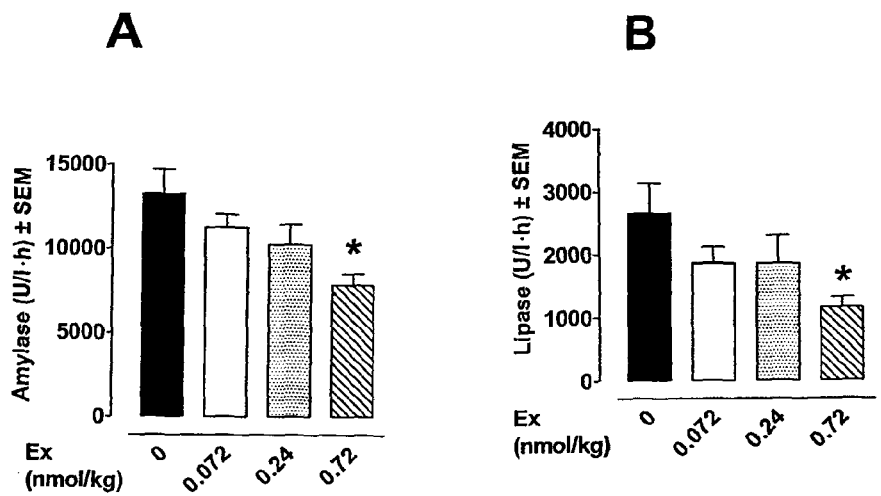
FIGS. 2A-B: Area under the curves ($AUC_{0-6h}$) for plasma amylase (FIG. 2A) and lipase (FIG. 2B) in normal HSD rats dosed with exenatide followed with chemically-induced acute pancreatitis.

The effects of acute exenatide administration on amylase and lipase release were studied in the caerulein and sodium taurocholate models of pancreatitis. Single injections of exenatide prior to induction of pancreatitis with caerulein produced dose-related decreases in amylase (FIG. 1A) and lipase (FIG. 1B) in HSD rats. However, exenatide did not affect amylase and lipase release in ZDF rats. In Wistar rats with sodium taurocholate-induced pancreatitis, twice daily dosing of exenatide for 48 hours did not change amylase or lipase concentrations. The corresponding AUCs calculated for both pancreatic enzymes in studies with all 3 rat models are shown in FIG. 2. In HSD rats, the highest dose of exenatide (0.72 nmol/kg/d) exhibited significantly lower values for amylase $AUC_{0-6h}$ (FIG. 2A) or lipase $AUC_{0-6h}$ (FIG. 2B) than treatment with vehicle ($p<0.05$). The effects of lower doses of exenatide did not differ from vehicle controls in this study and no significant differences for amylase or lipase AUCs were found for all doses of exenatide in caerulein-treated ZDF or sodium taurocholate-treated Wistar rats.

In a subsequent acute study in diabetic ob/ob mice, five hourly intraperitoneal injections of caerulein (10 µg/kg) induced dramatic increases of plasma amylase and lipase similarly to rat studies. A single injection of exenatide (5 nmol/kg) given 15 min prior to induction of pancreatitis had no effect on pancreatic enzymes (data not shown).

Figure 3:
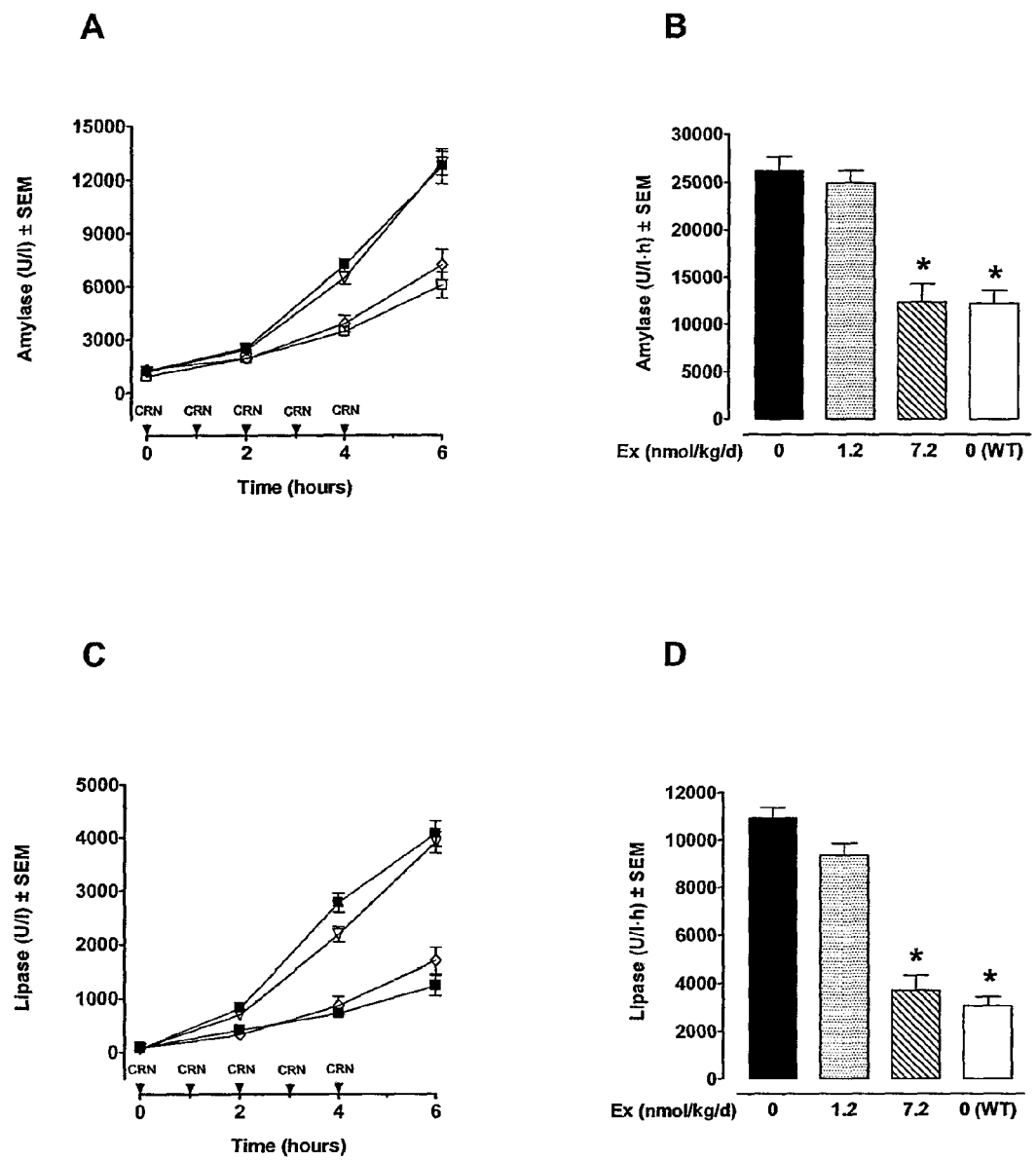
FIGS. 3A-D: Time course of plasma amylase (FIG. 3A) and lipase (FIG. 3C) during caerulein-induced pancreatitis in diabetic ob/ob mice treated with continuous subcutaneous infusion of different doses of exenatide ((1.2 (open triangles), 7.2 nmol/kg/d (open diamonds)) or with vehicle (black squares) for 4 weeks. Calculated 6-h plasma amylase (FIG. 3B) and lipase (FIG. 3D) areas under the curves. n=8-10 per group. *$p<0.05$ exenatide (7.2 nmol/kg/d) or WT vs vehicle-dosed ob/ob mice.

Effect of chronic dosing of exenatide on amylase and lipase on caerulein-induced pancreatitis in ob/ob mice: To examine whether exenatide affected pancreatitis-related endpoints in rodent models of diabetes after a longer exposure time, we administered caerulein following a 4-week subcutaneous infusion of exenatide (1.2 and 7.2 nmol/kg/d) in diabetic ob/ob mice. The time courses for plasma amylase and lipase concentrations and the corresponding $AUC_{0-6h}$ are shown in FIG. 3. Compared to vehicle treatment, exenatide at 7.2 nmol/kg/day significantly reduced plasma amylase (FIG. 3A and FIG. 3B) and lipase (FIG. 3C and FIG. 3D) responses to caerulein. Pancreatic enzyme excursions were similar in magnitude to those observed in normal wild-type mice without pancreatitis. Exenatide at a dose of 1.2 nmol/kg/day did not modify amylase or lipase levels.

Effects of exenatide on pancreatic weight: Pancreatic weight is used as an indicator of fluid retention and edema in experimental pancreatitis. In general, exenatide had no effect on pancreatic weight when administered acutely to rats or mice and did not affect pancreatic weight in sub-chronic studies in two strains of diabetic mice. Single doses of caerulein did not change pancreatic weight in normal HSD or diabetic ZDF rats, although five hourly injections of caerulein significantly increased pancreas weight in ob/ob mice ($p<0.01$). When exenatide was administered either prior (caerulein-treated HSD, ZDF rats or ob/ob mice) or during (sodium taurocholate-treated Wistar rat, caerulein-treated ob/ob mice) the induction of pancreatitis, exenatide did not modify pancreatic weight in any of the rodent models studied.

Effects of exenatide on inflammatory cytokines: To determine whether exenatide influences inflammatory mediators during experimental pancreatitis, we measured Il-1 β, Il-2, Il-6, MCP-1, IFN-γ, and TNF-α in the plasma from ob/ob mice at study end. In general, the cytokines Il-1 β, Il-2, and IFN-γ remained unchanged from the baseline levels during caerulein-induced pancreatitis and exenatide did not affect their plasma concentrations during either acute or sub-chronic administration. In contrast, Il-6 was dramatically increased after caerulein treatment ($p<0.01$) and was highly variable within treatment groups, although again exenatide had no statistically significant effect when administered either acutely or sub-chronically. A three-order of magnitude difference in IL-6 elevation was observed between WT and ob/ob mice, indicating that diabetic animals had a higher susceptibility to a pancreatic inflammatory response. Caerulein-administration also significantly induced MCP-1. Similarly to IL-6, MCP-1 concentrations were dramatically lower in WT mice than in diabetic mice. A single acute dose of exenatide did not affect MCP-1 induction; however, sub-chronic dosing with exenatide exhibited a trend towards attenuation of the caerulein-induced increase in MCP-1. TNF-α did not rise during experimental pancreatitis. However, similarly to MCP-1, it tended to be attenuated by sub-chronic treatment with exenatide.

Effects of exenatide on pancreas histology in mice and rats with acute pancreatitis: Histological analyzes revealed that caerulein did not cause significant changes in the pancreatic tissues of HSD or ZDF rats, whereas sodium taurocholate administration induced degenerative and inflammatory changes in the pancreas, including edema, vacuolation and necrosis of acinar cells, and neutrophilic infiltration. Exenatide did not affect the observed histology of pancreata from HSD or ZDF rats. However, in the pancreas after sodium taurocholate injury, exenatide at the highest dose (0.72 nmol/kg/d) lowered the severity of vacuolation and degeneration of acinar cells, the infiltration of inflammatory cells and necrosis in adipose tissue compared to vehicle-treated pancreata.

In ob/ob mice, caerulein also produced evident degenerative and inflammatory pathological changes in pancreata. Markedly fewer histological changes were observed in WT controls. Four-weeks of treatment with exenatide (7.2 nmol/kg/d) had subtle effects on pancreatic histology, decreasing the incidence and severity of caerulein-induced acute inflammation, vacuolation and acinar single cell necrosis compared with vehicle controls. In contrast, the low dose of exenatide did not affect histological evidence of pancreatitis. In general, the histological results for WT and ob/ob mice treated with exenatide were consistent with measurements of plasma amylase, lipase and inflammatory cytokines. They indicated an increased susceptibility to experimental pancreatitis in diabetic animals and beneficial effects of exenatide on pancreatitis-associated endpoints.

To determine whether exenatide affects pancreatic duct cell proliferation, we examined pancreata from ob/ob mice treated with exenatide for 4 weeks followed by caerulein-induced pancreatitis. Representative immunofluorescence images of ductal structures and replicating cells labeled with Ki-67 from WT controls, exenatide or vehicle treated ob/ob mice are shown in FIG. 6B. The rate of ductal cell proliferation was low (below 1%) and similar in all groups ($p<0.11$). Moreover, as shown in Table 5, an independent board-certified veterinary histopathologist found rare incidences of mild to moderate focal duct proliferation present in both the pancreata of WT mice not treated with exenatide and in ob/ob mice treated with high and low doses of exenatide.

Effect of exenatide on expression of genes associated with pancreatitis: The expression of genes known to be associated with pancreatitis (Reg3b, Egr1, Icam1, Il6, Ccl2 (encoding MCP-1), Nfkb1, Mpo and Vamp8) were studied in samples of fixed and sectioned pancreata. Consistent with biochemical studies of pancreatitis-associated inflammation, expression of the genes encoding MCP-1 and Il-6 was dramatically induced in pancreata of diabetic mice in comparison with those of WT controls. Exenatide did not modify expression of these two genes. Similarly, exenatide did not modify expression of Egr1, Nfkb1 or Vamp8. However, an exenatide dose-related induction of Reg3b expression was observed, which reached statistical difference for the high dose of exenatide (7.2 nmol/kg/d) compared with the vehicle treated diabetic control ($p<0.05$).

Discussion: The results of this study demonstrate that exenatide at acute or sub-chronic doses equivalent to approximately 30-fold effective clinical doses did not induce acute pancreatitis in normal or diabetic/obese rodents and did not increase the severity of chemically-induced pancreatitis. Furthermore, at the highest dose of exenatide tested, exenatide reduced amylase and lipase release in response to caerulein injury, and reduced histological evidence of pancreatic injury in sodium taurocholate-treated animals. A trend towards reduced MCP-1 production was observed, although production of other cytokines was not affected by exenatide. In general, the histological results for the pancreata of WT and ob/ob mice treated with exenatide were consistent with measurements of plasma amylase, lipase and inflammatory cytokines.

The baseline findings observed in the animal models of pancreatitis studied appear consistent with those of human pancreatitis. Diabetic and obese ZDF rats had elevated plasma amylase and lipase in comparison to non-diabetic counterparts, indicative of pancreatic injury. Likewise, ob/ob diabetic mice exhibited higher amylase concentrations than normal non-diabetic animals. Additionally, amylase and lipase responses to chemically-induced pancreatitis were greater in these mice than in normal wild type controls. These findings correlate with clinical reports, which described elevated amylase and lipase, and increased risk of acute pancreatitis in patients with type 2 diabetes or obesity.

The results of acute and sub-chronic exenatide administration at approximately 30-fold clinical doses in two rodent species did not provide evidence that exenatide induces or worsens pancreatitis in these species. In two mouse models of diabetes (ob/ob and HF-STZ), 4-weeks of continuous dosing with anti-diabetic doses of exenatide did not change baseline amylase or lipase plasma levels. There is a limited literature on pancreatic enzymes levels in animals dosed chronically with GLP-1 receptor agonists. In a recent paper, Nachnani et al., *Diabetologia*, 53(1):153-159 (2010) reported that exenatide at dose of 10 μg (2.4 nmol)/kg/d did not affect amylase when dosed for 75 days in normal Sprague-Dawley rats, which is consistent with our findings in diabetic mice. On the other hand, in their studies, exenatide showed a slight but significant effect on serum lipase levels. Usually, during pancreatitis, the concentration of pancreatic enzymes in the systemic circulation increases by orders of magnitude over normal levels. Therefore, a slight, although statistically significant, increase in lipase is unlikely to be physiologically important.

To better understand the role of exenatide in experimental pancreatitis, we studied acute and subchronic administration of exenatide in two models of different severities of the disease. Severity of pancreatitis was measured by amylase and lipase concentrations in plasma. In the most severe model of pancreatitis, induced by sodium taurocholate, exenatide did not modify amylase and lipase secretion during 48-h of observation. However, histopathological evaluation revealed that the highest dose of exenatide (0.72 nmol/kg/d) used in this study decreased pancreatitis-associated tissue damage. Surprisingly, in the caerulein-induced mild form of pancreatitis, single doses of exenatide attenuated amylase and lipase excursions. However, the same single dose of exenatide in caerulein-induced pancreatitis in diabetic ZDF rats did not affect pancreatic enzymes.

An extended duration of exenatide therapy might be required to improve pancreatitis in animals with diabetes. In ob/ob mice, when caerulein insult was applied at the end of sub-chronic treatment for 4 weeks, exenatide (7.2 nmol/kg/d) decreased amylase and lipase concentrations to the levels found in normal wild type controls. The lower dose of exenatide tested (2.4 nmol/kg/d) did not show such an effect, providing evidence that the effect is dose-dependent. These positive results were accompanied by the histological finding that less damage to pancreatic acinar cells occurred in animals treated with exenatide than in vehicle controls. Our results in diabetic mice are in contrast to observations in normal rats, where authors observed very subtle changes in exocrine cell size, rate of pyknotic nuclei or fibrosis in vascular or ductal walls with exenatide treatment.

Recently, increased ductal cell turnover and metaplasia were reported in diabetic transgenic HIP rats treated with DPPIV inhibitor sitagliptin, with one rat exhibiting the histological features of acute pancreatitis. The authors raised the question about plausible risk of long-term GLP-1-based therapy on development of a chronic pancreatitis In their studies, the DPP-IV inhibitor not a GLP-1 receptor agonist was used, and it is unlikely that endogenous GLP-1 can reach concentrations comparable to the therapeutic levels of GLP-1 receptor agonists seen in the clinic. Furthermore, DPP-4 inhibitors prevent the degradation of multiple signaling peptides, including Substance P, which is known to be involved in acute pancreatitis. Therefore, any conclusion about risks associated with exenatide therapy based on this data is debatable. In our studies, no significant increase in duct cell proliferation rate was observed after 4-weeks of continuous treatment with exenatide, and no differences in ductal morphology was found between exenatide and non-exenatide treated animals.

The results in these examples are consistent with previous explorations on the toxicology of exenatide. Extensive non-clinical toxicology assessments were undertaken to support the development and marketing of exenatide twice daily. Single-dose and repeated dose toxicology studies were conducted in mice, rats and monkeys with exenatide with the result that no drug-related effects on the exocrine pancreas were noted (data on-file). Carcinogenicity studies (2-years of treatment with exenatide) were also conducted in mice and rats and no drug-related pre-neoplastic changes or increased incidences of tumors in the exocrine pancreas were observed. Exenatide was also found to be devoid of mutagenic or clastogenic potential. Overall, data in the toxicology database indicated that the acute or chronic administration of exenatide was not associated with any drug-related adverse effects on the pancreas (including the exocrine pancreas). No pro-inflammatory, pre-neoplastic or neoplastic changes were observed when exenatide was administered for up to 9 months in monkeys and up to 2 years in rodents (mice and rats). In those studies, complete histopathological studies (including the pancreas) were conducted by an independent board-certified veterinary pathologist.

Since multiple measurements in several model systems demonstrated improvements in manifestations of pancreatitis with exenatide treatment, it is important to consider the mechanisms that may be responsible for the observed beneficial effects of exenatide in rodent models of pancreatitis. Firstly, cytoprotection via downregulation of apoptosis, upregulation of proliferation or neogenesis has been very well documented in multiple studies on pancreatic beta-cells.

Therefore it cannot be ruled out that exenatide can exert similar protective effects on acinar or ductal cells. Additionally, it has been shown that exenatide upregulated the expression of protective pancreatitis-associated gene Reg3b and similar results were obtained in the study. Moreover, it has been documented that adiponectin, which is increased in patients treated with exenatide, plays a protective role in caerulein-induced pancreatitis in mice.

Secondly, exenatide slows gastric emptying, affects antro-pyloro-duodenal motility and inhibits pancreatic bicarbonate and protein secretion. The exocrine pancreas is densely innervated and vascularized with neuronal and endothelial cells that express the GLP-1 receptor. Therefore central or peripheral direct or indirect neural regulation of exocrine secretion, vascular tone or permeability could be considered as a plausible factors contributing to the beneficial effects of exenatide on digestive enzyme secretion.

Finally, pancreatitis is associated with inflammation, which is manifested by elevated proinflammatory cytokines in plasma or pancreatic tissue. Exploratory data from our studies in ob/ob mice sub-chronically dosed with exenatide did not show any increase of several inflammatory mediators (Il-1 β, Il-2, IFN γ) as measured in plasma or at gene levels in the pancreas (Il-6, MCP-1, NF-κB). Moreover, some of them (Il-6, MCP-1) exhibited a trend to be downregulated in plasma. TNF-α is known to induce apoptosis in pancreatic β cells and exenatide directly antagonized this effect in vitro. We can speculate that observed decrease in TNF-α plasma levels in our study after the treatment with exenatide might exerted an additional anti-inflammatory effects. It remains to be demonstrated if these preliminary rodent results will translate to the clinical observations.

These results from studies in rodent models of diabetes, obesity, and chemically-induced pancreatitis suggest that exenatide might have beneficial effects on acute pancreatitis.

Example 2

The aim of this study was to characterize the effects of exenatide on exocrine pancreatic structure and function in ZDF rats treated chronically with exenatide at doses yielding plasma levels several fold higher than clinical exposure.

Rats were dosed subcutaneously with exenatide (6, 40, 250 µg/kg/d BID) or vehicle for 3 consecutive months. HbA1c, fasting serum lipase, amylase, glucose and insulin, body weight, and food consumption were measured monthly. Plasma exenatide levels were assessed at the beginning and end of the study. Pancreata were weighed and processed for histology. Morphometric analysis of duct cell proliferation and apoptosis was performed via immunostaining with cytokeratin (duct), Ki-67 (proliferation) and TUNEL (apoptosis). The same endpoints were measured after 1-month recovery in a subset of animals from each group. Results are presented as mean±SD. The differences between groups were considered statistically significant when $p<0.05$ with ANOVA.

As expected, exenatide improved glycemic endpoints including a decrease in HbA1c and glucose, and an increase in insulin and islet size, in comparison to vehicle. Exenatide had no effect on lipase. Treatment with exenatide was associated with a small but significant increase in amylase levels (U/L) (exenatide 6 µg/kg/d=3266±391, exenatide 40 µg/kg/d=3517±404, exenatide 250 µg/kg/d=3286±322) vs. control (2706±289, $p<0.05$) at 3 months. There was no significant difference between all groups in amylase (U/L) at the end of the recovery period (exenatide 6 µg/kg/d=3310±343, exenatide 40 µg/kg/d=3376±330, exenatide 250 µg/kg/d=3261±473, control=3395±1016). At the beginning of the study, the area under the exenatide plasma concentration-time curve ($AUC_{0-8h}$) ranged from 1 to 3 ng·h/mL and the maximal concentration ($C_{max}$) ranged from 1 to 43 ng/mL. These values were higher than $AUC_{0-8h}$ and $C_{max}$ seen with the highest recommended dose of exenatide in humans (20 µg/d) by approximately 1-to 61-fold and 5- to 205-fold, respectively. $AUC_{0-8h}$ increased substantially after 3 months with the accumulation ratio ranging from 2.7 to 4.4. Exenatide improved survival of animals (100% survival in all treatment groups) in comparison to vehicle controls (60%) during the dosing period. There was no exenatide-related difference in absolute or relative pancreatic weight. Histological analysis revealed no changes in pancreatic exocrine tissue morphology in animals treated with exenatide. Ductal cell proliferation rate was low (<0.15%) and similar for all groups at the end of the treatment and after the recovery period. There was no significant difference in ductal cell apoptosis between all groups.

To summarize, the experiment showed that long-term exposure to exenatide at plasma levels several fold higher than therapeutic levels in humans resulted in the metabolic benefits and improved animal survival, and did not adversely affect exocrine pancreas structure and function.

What is claimed is:

1. A method for treating acute pancreatitis in a human in need thereof comprising administering to the human a therapeutically effective amount of exenatide to treat acute pancreatitis.

2. A method for treating pancreatitis in a patient in need thereof comprising administering to the patient a therapeutically effective amount of a GLP-1 receptor agonist to treat pancreatitis.

3. The method of claim 2, wherein the pancreatitis is acute pancreatitis.

4. The method of claim 3, wherein the acute pancreatitis is acute hemorrhagic pancreatitis.

5. The method of claim 3, wherein the acute pancreatitis is acute necrotizing pancreatitis.

6. The method of claim 3, wherein the acute pancreatitis is acute hemorrhagic-necrotizing pancreatitis.

7. The method of claim 2, wherein the GLP-1 receptor agonist is exenatide.

8. The method of claim 2, wherein the GLP-1 receptor agonist is a peptide having at least 75% sequence identity to exenatide.

9. The method of claim 2, wherein the GLP-1 receptor agonist is a peptide having at least 90% sequence identity to exenatide.

10. The method of claim 2, wherein the GLP-1 receptor agonist is lixisenatide.

11. The method of claim 2, wherein the GLP-1 receptor agonist is liraglutide.

12. The method of claim 2, wherein the GLP-1 receptor agonist is dulaglutide.

13. The method of claim 2, wherein the GLP-1 receptor agonist is albiglutide or taspoglutide.

14. The method of claim 2, wherein the GLP-1 receptor agonist is lixisenatide; CJC-1134; SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58 or SEQ ID NO:59.

15. The method of claim 2, wherein the GLP-1 receptor agonist is LY2428757; SEQ ID NO:22; SEQ ID NO:23; SEQ ID NO:24; HXaa$_8$EGTFTSDVSSYLE-Xaa$_{22}$Xaa$_{23}$AAKEFIXaa$_{30}$WLXaa$_{33}$Xaa$_{34}$GXaa$_{36}$Xaa$_{37}$ (SEQ ID NO: 25); wherein Xaa$_8$ is A, V, or G; Xaa$_{22}$ is G, K, or E; Xaa$_{23}$ is Q or K; Xaa$_{30}$ is A or E; Xaa$_{33}$ is V or K; Xaa$_{34}$ is K, N, or R; Xaa$_{36}$ is R or G; and Xaa$_{37}$ is G, H, P, or absent; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:43; SEQ ID NO:60; SEQ ID NO:61; SEQ ID NO:62; or SEQ ID NO:63.

16. The method of claim 1, wherein the acute pancreatitis is acute hemorrhagic pancreatitis.

17. The method of claim 1, wherein the acute pancreatitis is acute necrotizing pancreatitis.

18. The method of claim 1, wherein the acute pancreatitis is acute hemorrhagic-necrotizing pancreatitis.

\* \* \* \* \*

SEQUENCE LISTING

<160> NUMBER OF SEQ ID NOS: 63

<210> SEQ ID NO 1
<211> LENGTH: 39
<212> TYPE: PRT
<213> ORGANISM: Heloderma suspectum
<220> FEATURE:
<223> OTHER INFORMATION: C-term amidated

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

-continued

```
<210> SEQ ID NO 2
<211> LENGTH: 39
<212> TYPE: PRT
<213> ORGANISM: Heloderma horridum
<220> FEATURE:
<223> OTHER INFORMATION: C-term amidated

<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Homo sapiens
<220> FEATURE:
<223> OTHER INFORMATION: C-term may or may not be amidated

<400> SEQUENCE: 3

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 4

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 5

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn Gly Gly Pro Ser
            20                  25                  30

Ser Gly Ala Pro Pro Pro Ser
```

```
<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 7

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 8

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 9

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn Gly Gly
            20                  25                  30

<210> SEQ ID NO 10
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term may or may not be amidated

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term may or may not be amidated

<400> SEQUENCE: 11

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term may or may not be amidated

<400> SEQUENCE: 12

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term may or may not be amidated

<400> SEQUENCE: 13

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 14
<211> LENGTH: 39
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: C-term may or may not be amidated

<400> SEQUENCE: 14

His Gly Glu Gly Thr Phe Thr Ser Asp Leu Ser Lys Gln Leu Glu Glu
1               5                  10                  15

Lys Ala Ala Lys Glu Phe Ile Glu Phe Leu Lys Gln Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 15

His Gly Glu Gly Thr Phe Thr Ser Asp Leu Ser Lys Gln Leu Glu Glu
1               5                  10                  15

Lys Ala Ala Lys Glu Phe Ile Glu Trp Leu Lys Gln Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Octyl-Gly
<220> FEATURE:
<223> OTHER INFORMATION: C-term may or may not be amidated

<400> SEQUENCE: 16

His Gly Glu Gly Thr Phe Thr Ser Asp Leu Ser Lys Gln Gly Glu Glu
1               5                  10                  15

Glu Ala Val Arg Leu Phe Ile Glu Trp Leu Lys Gln Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Octyl-Gly
<220> FEATURE:
<223> OTHER INFORMATION: C-term may or may not be amidated

<400> SEQUENCE: 17

-continued

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Ser
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 18

His Gly Glu Phe Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 19

His Gly Glu Phe Thr Phe Thr Ser Asp Leu Ser Lys Gln Leu Glu Glu
1               5                   10                  15

Lys Ala Ala Lys Glu Phe Ile Glu Trp Leu Lys Gln Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 20

His Gly Glu Gly Thr Phe Thr Ser Asp Leu Val Lys Ile Leu Glu Ala
1               5                   10                  15

Glu Ala Val Arg Lys Phe Ile Glu Phe Leu Lys Asn Gly Gly Pro Ser
            20                  25                  30

Ser Gly Ala Pro Pro Pro Ser
        35

<210> SEQ ID NO 21
<211> LENGTH: 40
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 22
<211> LENGTH: 31
<212> TYPE: PRT
<213> ORGANISM: Homo sapiens
<220> FEATURE:
<223> OTHER INFORMATION: C-term may or may not be amidated

<400> SEQUENCE: 22

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 23

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<223> OTHER INFORMATION: C-term may or may not be amidated

<400> SEQUENCE: 24

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg
            20                  25                  30
```

-continued

```
<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ala, Val, or Gly
<220> FEATURE:
<221> NAME/KEY: MOD_RES
<222> LOCATION: (16)..(16)
<223> OTHER INFORMATION: Gly, Lys, or Glu
<220> FEATURE:
<221> NAME/KEY: MOD_RES
<222> LOCATION: (17)..(17)
<223> OTHER INFORMATION: Gln or Lys
<220> FEATURE:
<221> NAME/KEY: MOD_RES
<222> LOCATION: (24)..(24)
<223> OTHER INFORMATION: Ala or Glu
<220> FEATURE:
<221> NAME/KEY: MOD_RES
<222> LOCATION: (27)..(27)
<223> OTHER INFORMATION: Val or Lys
<220> FEATURE:
<221> NAME/KEY: MOD_RES
<222> LOCATION: (28)..(28)
<223> OTHER INFORMATION: Lys, Asn, or Arg
<220> FEATURE:
<221> NAME/KEY: MOD_RES
<222> LOCATION: (30)..(30)
<223> OTHER INFORMATION: Arg or Gly
<220> FEATURE:
<221> NAME/KEY: MOD_RES
<222> LOCATION: (31)..(31)
<223> OTHER INFORMATION: Gly, His, Pro, or not present

<400> SEQUENCE: 25

His Xaa Glu Gly Thr Phe Thr Ser Asp Val Ser Ser Tyr Leu Glu Xaa
 1               5                  10                  15

Xaa Ala Ala Lys Glu Phe Ile Xaa Trp Leu Xaa Xaa Gly Xaa Xaa
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 26

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Arg Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 27
```

```
His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 28

His Ala Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg Gly
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 29

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 30

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 31

His Gly Glu Gly Thr Phe Thr Ser Asp Val Ser Ser Tyr Leu Glu Glu
1               5                   10                  15
```

Gln Ala Ala Lys Glu Phe Ile Ala Trp Leu Lys Asn Gly Gly Gly
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 32

His Val Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Gly
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 33

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 34

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
            20                  25                  30

<210> SEQ ID NO 35
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 35

His Gly Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Pro
            20                  25                  30

```
<210> SEQ ID NO 36
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 36

His Val Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Pro
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 37

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 38

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 39

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Asn Gly Gly
            20                  25                  30

<210> SEQ ID NO 40
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 40

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Asn Gly Gly
            20                  25                  30

<210> SEQ ID NO 41
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Pro or Glu
<220> FEATURE:
<221> NAME/KEY: MOD_RES
<222> LOCATION: (17)..(17)
<223> OTHER INFORMATION: Phe, Val, or Ala
<220> FEATURE:
<221> NAME/KEY: MOD_RES
<222> LOCATION: (18)..(18)
<223> OTHER INFORMATION: Leu, Glu, or Ala
<220> FEATURE:
<221> NAME/KEY: MOD_RES
<222> LOCATION: (80)..(80)
<223> OTHER INFORMATION: Asn or Ala
<220> FEATURE:
<221> NAME/KEY: MOD_RES
<222> LOCATION: (230)..(230)
<223> OTHER INFORMATION: May or may not be present

<400> SEQUENCE: 41

Ala Glu Ser Lys Tyr Gly Pro Pro Cys Pro Pro Cys Pro Ala Pro Xaa
1               5                   10                  15

Xaa Xaa Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Xaa
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190
```

```
Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Lys
225             230

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This region may encompass 1 to 6 "Gly Gly Gly
      Gly Ser" repeating units
<220> FEATURE:
<223> OTHER INFORMATION: see specification as filed for detailed
      description of substitutions and preferred embodiments

<400> SEQUENCE: 42

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser
            20                  25                  30

<210> SEQ ID NO 43
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65              70                  75                  80

Met Ile Ser Arg Thr Pro Glu Val Thr Cys Val Val Val Asp Val Ser
            85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
            130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
            165                 170                 175

Val Tyr Thr Leu Pro Pro Ser Gln Glu Glu Met Thr Lys Asn Gln Val
```

```
                        180                 185                 190
Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
        210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
        275

<210> SEQ ID NO 44
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ala, Gly, Val, Leu, Ile, Ser, or Thr
<220> FEATURE:
<221> NAME/KEY: MOD_RES
<222> LOCATION: (16)..(16)
<223> OTHER INFORMATION: Gly, Glu, Asp, or Lys
<220> FEATURE:
<221> NAME/KEY: MOD_RES
<222> LOCATION: (27)..(27)
<223> OTHER INFORMATION: Val or Ile
<220> FEATURE:
<223> OTHER INFORMATION: C-term OH or NH2
<220> FEATURE:
<223> OTHER INFORMATION: see specification as filed for detailed
      description of substitutions and preferred embodiments

<400> SEQUENCE: 44

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Xaa Lys Gly Gly Pro Ser
            20                  25                  30

Ser Gly Ala Pro Pro Pro Cys Cys
        35                  40

<210> SEQ ID NO 45
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated
<220> FEATURE:
<223> OTHER INFORMATION: see specification as filed for detailed
      description of substitutions and preferred embodiments

<400> SEQUENCE: 45

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Ala Pro Pro Pro Cys Cys
```

```
<210> SEQ ID NO 46
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: N-epsilon-(17-carboxyheptadecanoic acid)Lys
<220> FEATURE:
<223> OTHER INFORMATION: C-term may or may not be amidated

<400> SEQUENCE: 46

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: N-epsilon-(17-carboxyheptadecanoyl)Lys
<220> FEATURE:
<223> OTHER INFORMATION: C-term may or may not be amidated

<400> SEQUENCE: 47

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Lys
            20                  25                  30

Ser Gly Ala Pro Pro Pro Ser
        35

<210> SEQ ID NO 48
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: N-epsilon-(17-carboxyheptadecanoyl)Lys
<220> FEATURE:
<223> OTHER INFORMATION: C-term may or may not be amidated

<400> SEQUENCE: 48

Gly Glu Gly Thr Phe Thr Ser Asp Leu Ser Lys Gln Met Glu Glu Glu
1               5                   10                  15

Ala Val Lys Leu Phe Ile Glu Trp Leu Lys Asn Gly Gly Pro Ser Ser
            20                  25                  30

Gly Ala Pro Pro Pro Ser
        35
```

```
<210> SEQ ID NO 49
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (32)..(32)
<223> OTHER INFORMATION: N-epsilon-(17-carboxyheptadecanoyl)Lys
<220> FEATURE:
<223> OTHER INFORMATION: C-term may or may not be amidated

<400> SEQUENCE: 49

His Gly Glu Gly Thr Phe Thr Ser Asp Leu Ser Arg Gln Xaa Glu Glu
1               5                   10                  15

Glu Ala Val Arg Leu Phe Ile Glu Trp Leu Arg Asn Gly Gly Pro Lys
            20                  25                  30

Ser Gly Ala Pro Pro Ser
        35

<210> SEQ ID NO 50
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: N-epsilon-(19-carboxynonadecanoylamino)Lys
<220> FEATURE:
<223> OTHER INFORMATION: C-term may or may not be amidated

<400> SEQUENCE: 50

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Ser
        35

<210> SEQ ID NO 51
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: N-epsilon-(15-carboxypentadecanoylamino)Lys
<220> FEATURE:
<223> OTHER INFORMATION: C-term may or may not be amidated

<400> SEQUENCE: 51

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Ser
```

35

```
<210> SEQ ID NO 52
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: N-epsilon-(13-carboxytridecanoylamino)Lys
<220> FEATURE:
<223> OTHER INFORMATION: C-term may or may not be amidated

<400> SEQUENCE: 52

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 53
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: N-epsilon-(11-carboxyundecanoylamino)Lys
<220> FEATURE:
<223> OTHER INFORMATION: C-term may or may not be amidated

<400> SEQUENCE: 53

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 54
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Lys(epsilon-maleimidopropionic acid)
<220> FEATURE:
<223> OTHER INFORMATION: C-term may or may not be amidated

<400> SEQUENCE: 54

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40
```

```
<210> SEQ ID NO 55
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Lys(epsilon-[2-(2-amino)ethoxy]ethoxy acetic
      acid-[2-(2-amino)ethoxy]ethoxy acetic acid-maleimidopropionic
      acid)
<220> FEATURE:
<223> OTHER INFORMATION: C-term may or may not be amidated

<400> SEQUENCE: 55

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 56
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Lys(epsilon-[2-(2-amino)ethoxy]ethoxy acetic
      acid-maleimidopropionic acid)
<220> FEATURE:
<223> OTHER INFORMATION: C-term may or may not be amidated

<400> SEQUENCE: 56

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 57
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Lys(epsilon-maleimidopropionic acid)-albumin
<220> FEATURE:
<223> OTHER INFORMATION: C-term may or may not be amidated

<400> SEQUENCE: 57

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40
```

```
<210> SEQ ID NO 58
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Lys(epsilon-[2-(2-amino)ethoxy]ethoxy acetic
      acid-[2-(2-amino)ethoxy]ethoxy acetic acid-maleimidopropionic
      acid)-albumin
<220> FEATURE:
<223> OTHER INFORMATION: C-term may or may not be amidated

<400> SEQUENCE: 58

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 59
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Lys(epsilon-[2-(2-amino)ethoxy]ethoxy acetic
      acid-maleimidopropionic acid)-albumin
<220> FEATURE:
<223> OTHER INFORMATION: C-term may or may not be amidated

<400> SEQUENCE: 59

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 60
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term may or may not be amidated

<400> SEQUENCE: 60

Ala Glu Gly Thr Phe Thr Ser Asp Val Ser Ser Tyr Leu Glu Gly Gln
1               5                   10                  15

Ala Ala Arg Glu Phe Ile Ala Trp Leu Val Lys Gly Arg Gly
            20                  25                  30

<210> SEQ ID NO 61
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Lys(N-epsilon-octanoyl)
<220> FEATURE:
<223> OTHER INFORMATION: C-term may or may not be amidated

<400> SEQUENCE: 61

Ala Glu Gly Thr Phe Thr Ser Asp Val Ser Ser Tyr Leu Glu Gly Gln
1               5                   10                  15

Ala Ala Arg Glu Phe Ile Ala Trp Leu Val Lys Gly Arg Gly
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Lys(N-epsilon(omega-carboxypentadecanoyl)
<220> FEATURE:
<223> OTHER INFORMATION: C-term may or may not be amidated

<400> SEQUENCE: 62

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys
            20                  25                  30
```